United States Patent
Chiesl et al.

(10) Patent No.: US 9,334,491 B2
(45) Date of Patent: May 10, 2016

(54) SYSTEMS AND METHODS FOR ISOLATING NUCLEIC ACIDS FROM CELLULAR SAMPLES

(71) Applicant: IBIS BIOSCIENCES, INC., Carlsbad, CA (US)

(72) Inventors: Thomas N. Chiesl, Hurcules, CA (US); Michelle Toro, Carlsbad, CA (US); Steven Gerald Haupt, San Diego, CA (US)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 0 days.

(21) Appl. No.: 14/367,776

(22) PCT Filed: Dec. 21, 2012

(86) PCT No.: PCT/US2012/071304
§ 371 (c)(1),
(2) Date: Jun. 20, 2014

(87) PCT Pub. No.: WO2013/096799
PCT Pub. Date: Jun. 27, 2013

(65) Prior Publication Data
US 2015/0184148 A1 Jul. 2, 2015

Related U.S. Application Data

(60) Provisional application No. 61/579,393, filed on Dec. 22, 2011.

(51) Int. Cl.
*C07H 21/00* (2006.01)
*C12Q 1/68* (2006.01)
(Continued)

(52) U.S. Cl.
CPC .............. *C12N 15/1006* (2013.01); *C12N 1/06* (2013.01); *C12N 1/066* (2013.01); *C12N 15/10* (2013.01); *C12N 15/1003* (2013.01); *C12Q 1/689* (2013.01); *C12Q 1/6895* (2013.01)

(58) Field of Classification Search
CPC ........................... C12N 15/1006; C12Q 1/6806
USPC ........................ 536/25.4, 25.41; 435/6.1, 91.1
See application file for complete search history.

(56) References Cited

U.S. PATENT DOCUMENTS 4,683,195 A  7/1987 Mullis et al.
4,683,202 A  7/1987 Mullis
(Continued)

FOREIGN PATENT DOCUMENTS

EP  0684315 A1  11/1995
WO  WO-0018957 A1  4/2000
WO  WO-2006084132 A2  8/2006

OTHER PUBLICATIONS

Adessi C., et al., "Solid Phase DNA Amplification: Characterisation of Primer Attachment and Amplification Mechanisms," Nucleic Acids Research, 2000, vol. 28 (20), pp. E87.
(Continued)

*Primary Examiner* — Jezia Riley
(74) *Attorney, Agent, or Firm* — David A. Casimir; Casimir Jones, S.C.

(57) ABSTRACT

The present disclosure relates to systems and methods for nucleic acid isolation from cellular samples. In particular, the present disclosure provides systems and methods for lysing cells and recovering nucleic acids.

11 Claims, 7 Drawing Sheets

(51) Int. Cl.
  *C12N 15/10* (2006.01)
  *C12N 1/06* (2006.01)

(56) References Cited

U.S. PATENT DOCUMENTS

| | | | |
|---|---|---|---|
| 4,800,159 | A | 1/1989 | Mullis et al. |
| 4,935,342 | A | 6/1990 | Seligson et al. |
| 4,965,188 | A | 10/1990 | Mullis et al. |
| 5,130,238 | A | 7/1992 | Malek et al. |
| 5,270,184 | A | 12/1993 | Walker et al. |
| 5,283,174 | A | 2/1994 | Arnold, Jr. et al. |
| 5,399,491 | A | 3/1995 | Kacian et al. |
| 5,455,166 | A | 10/1995 | Walker |
| 5,480,784 | A | 1/1996 | Kacian et al. |
| 5,643,767 | A | 7/1997 | Fischetti et al. |
| 5,695,934 | A | 12/1997 | Brenner |
| 5,710,029 | A | 1/1998 | Ryder et al. |
| 5,714,330 | A | 2/1998 | Brenner et al. |
| 5,750,341 | A | 5/1998 | Macevicz |
| 5,807,527 | A | 9/1998 | Burgoyne |
| 5,814,447 | A | 9/1998 | Ishiguro et al. |
| 5,824,518 | A | 10/1998 | Kacian et al. |
| 5,912,148 | A | 6/1999 | Eggerding |
| 5,925,517 | A | 7/1999 | Tyagi et al. |
| 5,928,862 | A | 7/1999 | Morrison |
| 6,130,073 | A | 10/2000 | Eggerding |
| 6,150,097 | A | 11/2000 | Tyagi et al. |
| 6,168,922 | B1 | 1/2001 | Harvey et al. |
| 6,210,891 | B1 | 4/2001 | Nyren et al. |
| 6,258,568 | B1 | 7/2001 | Nyren |
| 6,303,305 | B1 | 10/2001 | Wittwer et al. |
| 6,306,597 | B1 | 10/2001 | Macevicz |
| 6,432,360 | B1 | 8/2002 | Church |
| RE37,891 | E | 10/2002 | Collins et al. |
| 6,485,944 | B1 | 11/2002 | Church et al. |
| 6,511,803 | B1 | 1/2003 | Church et al. |
| 6,534,274 | B2 | 3/2003 | Becker et al. |
| 6,541,205 | B1 | 4/2003 | Yokoyama et al. |
| 6,787,308 | B2 | 9/2004 | Balasubramanian et al. |
| 6,818,395 | B1 | 11/2004 | Quake et al. |
| 6,833,246 | B2 | 12/2004 | Balasubramanian |
| 6,911,345 | B2 | 6/2005 | Quake et al. |
| 6,969,488 | B2 | 11/2005 | Bridgham et al. |
| 7,108,974 | B2 | 9/2006 | Ecker et al. |
| 7,115,400 | B1 | 10/2006 | Adessi et al. |
| 7,169,560 | B2 | 1/2007 | Lapidus et al. |
| 7,282,337 | B1 | 10/2007 | Harris |
| 7,329,492 | B2 | 2/2008 | Hardin et al. |
| 7,482,120 | B2 | 1/2009 | Buzby |
| 7,501,245 | B2 | 3/2009 | Quake et al. |
| 8,017,322 | B2 | 9/2011 | Ecker et al. |
| 8,017,743 | B2 | 9/2011 | Ecker et al. |
| 2005/0042638 | A1 | 2/2005 | Arnold et al. |
| 2005/0130173 | A1 | 6/2005 | Leamon et al. |
| 2006/0046265 | A1 | 3/2006 | Becker et al. |
| 2006/0148021 | A1 | 7/2006 | Herbert |
| 2009/0026082 | A1 | 1/2009 | Rothberg et al. |
| 2009/0035777 | A1 | 2/2009 | Kokoris et al. |
| 2009/0127589 | A1 | 5/2009 | Rothberg et al. |
| 2010/0137143 | A1 | 6/2010 | Rothberg et al. |
| 2010/0188073 | A1 | 7/2010 | Rothberg et al. |
| 2010/0197507 | A1 | 8/2010 | Rothberg et al. |
| 2010/0301398 | A1 | 12/2010 | Rothberg et al. |
| 2011/0256566 | A1 | 10/2011 | Schweigert |

OTHER PUBLICATIONS

Astier Y., et al., "Toward Single Molecule DNA Sequencing: Direct Identification of Ribonucleoside and Deoxyribonucleoside 5'-monophosphates by Using an Engineered Protein Nanopore Equipped with a Molecular Adapter," Journal of the American Chemical Society, 2006, vol. 128 (5), pp. 1705-1710.
Bennett S.T., et al., "Toward the 1,000 Dollars Human Genome," Pharmacogenomics, 2005, vol. 6 (4), pp. 373-382.
Branton D., et al., "The Potential and Challenges of Nanopore Sequencing," Nature Biotechnology, 2008, vol. 26 (10), pp. 1146-1153.
Brenner S., et al., "Gene Expression Analysis by Massively Parallel Signature Sequencing (MPSS) on Microbead Arrays," Nature Biotechnology, 2000, vol. 18 (6), pp. 630-634.
Co-pending U.S. Appl. No. 11/671,956, filed Feb. 6, 2007.
Co-pending U.S. Appl. No. 11/781,166, filed Jul. 20, 2007.
Dickinson J.H., et al., "The Direct Application of the Polymerase Chain Reaction to Dna Extracted from Foods," Letters in Applied Microbiology, 1995, vol. 20 (4), pp. 212-216.
Drmanac S., et al., "Accurate Sequencing by Hybridization for DNA Diagnostics and Individual Genomics," Nature Biotechnology, 1998, vol. 16 (1), pp. 54-58.
Eid J., et al., "Real-time Dna Sequencing from Single Polymerase Molecules," Science, 2009, vol. 323 (5910), pp. 133-138.
Guatelli J.C., et al., "Isothermal, in Vitro Amplification of Nucleic Acids by a Multienzyme Reaction Modeled after Retroviral Replication," Proceedings of the National Academy of Sciences, 1990, vol. 87 (5), pp. 1874-1878.
Harris T.D., et al., "Single-molecule Dna Sequencing of a Viral Genome," Science, 2008, vol. 320 (5872), pp. 106-109.
International Search Report and Written Opinion for Application No. PCT/US12/71304, mailed on Apr. 19, 2013, 20 pages.
International Search Report for Application No. PCT/US2012/071304, mailed on Apr. 19, 2013, 1 pages.
Kato K., "Impact of the Next Generation Dna Sequencers," International Journal of Clinical and Experimental Medicine, 2009, vol. 2 (2), pp. 193-202.
Korlach J., et al., "Selective Aluminum Passivation for Targeted Immobilization of Single DNA Polymerase Molecules in Zero-Mode Waveguide Nanostructures," Proceedings of the National Academy of Sciences, 2008, vol. 105 (4), pp. 1176-1181.
Kwoh D.Y., et al., "Transcription-Based Amplification System and Detection of Amplified Human Immunodeficiency Viru: Type 1 with a Bead-Based Sandwixh Hybridization Format," Proceeding of the National Academy of Sciences of the USA, 1989, vol. 86 (4), pp. 1173-1177.
Levene M.J., et al., "Zero-mode Waveguides for Single-molecule Analysis at High Concentrations," Science, 2003, vol. 299 (5607), pp. 682-686.
Lizardi P.M., et al., "Exponential Amplification of Recombinant—RNA Hybridization Probes," Bio/Technology, 1988, vol. 6, pp. 1197-1202.
MacLean D., et al., "Application of 'next-generation' Sequencing Technologies to Microbial Genetics," Nature Reviews Microbiology, 2009, vol. 7 (4), pp. 287-296.
Margulies M., et al., "Genome Sequencing in Microfabricated High-Density Picolitre Reactors," Nature, 2005, vol. 437 (7057), pp. 376-380.
Maxam A.M., et al., "A New Method for Sequencing Dna," Proceedings of the National Academy of Sciences of the United States of America, 1977, vol. 74 (2), pp. 560-564.
Mitra R.D., et al., "Fluorescent in Situ Sequencing on Polymerase Colonies," Analytical Biochemistry, 2003, vol. 320 (1), pp. 55-65.
Morozova O., et al., "Applications of Next-generation Sequencing Technologies in Functional Genomics," Genomics, 2008, vol. 92 (5), pp. 255-264.
Mullis K.B., et al., "Specific Synthesis of Dna in Vitro Via a Polymerase-catalyzed Chain Reaction," Methods in Enzymology, 1987, vol. 155, pp. 335-350.
Murakawa G. J., et al., "Direct detection of HIV-1 RNA from AIDS and ARC patient samples", DNA., 1988, 7 (4), 287-295.
Pennisi E., "Genomics. Semiconductors Inspire New Sequencing Technologies," Science, 2010, vol. 327 (5970), pp. 1190.
Persing, "In Vitro Nucleic Acid Amplification Techniques," Diagnostic Molecular Microbiology, 1993, pp. 51-77.
Ronaghi M., et al., "Real-time Dna Sequencing Using Detection of Pyrophosphate Release," Analytical Biochemistry, 1996, vol. 242 (1), pp. 84-89.
Ruparel H., et al., "Design and Synthesis of a 3'-o-allyl Photocleavable Fluorescent Nucleotide as a Reversible Terminator for Dna (56) References Cited

OTHER PUBLICATIONS

Sequencing by Synthesis," Proceedings of the National Academy of Sciences of the United States of America, 2005, vol. 102 (17), pp. 5932-5937.

Sanger F., et al., "DNA Sequencing with Chain-Terminating Inhibitors," Proceedings of the National Academy of Sciences, 1977, vol. 74 (12), pp. 5463-5467.

Shendure J., et al., "Accurate Multiplex Polony Sequencing of an Evolved Bacterial Genome," Science, 2005, vol. 309 (5741), pp. 1728-1732.

Sikkema J., et al., "Interactions of Cyclic Hydrocarbons with Biological Membranes," The Journal of Biological Chemistry, 1994, vol. 269 (11), pp. 8022-8028.

Voelkerding K.V., et al., "Next-Generation Sequencing: from Basic Research to Diagnostics," Clinical Chemistry, 2009, vol. 55 (4), pp. 641-658.

Walker G.T., et al., "Isothermal in Vitro Amplification of DNA by a Restriction Enzyme/DNA Polymerase System," Proceedings of the National Academy of Sciences, 1992, vol. 89 (1) pp. 392-396.

Weiss R., "Hot Prospect for New Gene Amplifier," Science, 1991, vol. 254 (5036), pp. 1292-1293.

SYSTEMS AND METHODS FOR ISOLATING NUCLEIC ACIDS FROM CELLULAR SAMPLES

CROSS REFERENCE TO RELATED APPLICATIONS

The present application claims priority to U.S. Provisional Patent Application 61/579,393, filed Dec. 22, 2011, which is incorporated by reference in its entirety.

FIELD OF INVENTION

The present disclosure relates to systems and methods for nucleic acid isolation from cellular samples. In particular, the present disclosure provides systems and methods for lysing cells and recovering nucleic acids.

BACKGROUND

Nucleic acids found in cells can be deoxyribonucleic acid or ribonucleic acid and can be genomic DNA, extrachromosomal DNA (e.g. plasmids and episomes), mitochondrial DNA, messenger RNA and transfer RNA. Nucleic acids can also be foreign to the host and contaminate a cell as an infectious agent, e.g. bacteria, viruses, fungi or single celled organisms and infecting multicellular organisms (parasites). Recently, detection and analysis of the presence of nucleic acids has become important for the identification of single nucleotide polymorphisms (SNPs), chromosomal rearrangements and the insertion of foreign genes. These include infectious viruses, e.g. HIV and other retroviruses, jumping genes, e.g. transposons, and the identification of nucleic acids from recombinantly engineered organisms containing foreign genes, e.g. Roundup Ready™ plants.

The analysis of nucleic acids has a wide array of uses. For example, the presence of a foreign agent can be used as a medical diagnostic tool. The identification of the genetic makeup of cancerous tissues can also be used as a medical diagnostic tool, confirming that a tissue is cancerous, and determining the aggressive nature of the cancerous tissue. Chromosomal rearrangements, SNPs and abnormal variations in gene expression can be used as a medical diagnostic for particular disease states. Further, genetic information can be used to ascertain the effectiveness of particular pharmaceutical drugs, known as the field of pharmacogenomics. Genetic variations between humans and between domestic animals can also be ascertained by DNA analysis. This is used in fields including forensics, paternity testing and animal husbandry.

Methods of extracting nucleic acids from cells are well known to those skilled in the art. A cell wall can be weakened by a variety of methods, permitting the nucleic acids to extrude from the cell and permitting its further purification and analysis. The specific method of nucleic acid extraction is dependent on the type of nucleic acid to be isolated, the type of cell, and the specific application used to analyze the nucleic acid. Many methods of isolating DNA are known to those skilled in the art, see for example the general reference Sambrook and Russell, 2001, "Molecular Cloning: A Laboratory Manual". For example, the prior art contains examples of chemically-impregnated and dehydrated solid-substrates for the extraction and isolation of DNA from bodily fluids that employ lytic salts and detergents and which contain additional reagents for long-term storage of DNA samples e.g. U.S. Pat. No. 5,807,527 detailing FTA paper and U.S. Pat. No. 6,168,922 detailing Isocard Paper. The prior art also contains examples of particle separation methods, e.g. U.S. RE 37,891.

Methods of isolating RNA, particularly messenger RNA (mRNA) are well known to those skilled in the art. Typically, cell disruption is performed in the presence of strong protein denaturing solutions, which inactivate RNAses during the RNA isolation procedure. RNA is then isolated using differential ethanol precipitation with centrifugation. As is well known, RNA is extremely labile and is sensitive to alkaline conditions, as well as RNAses, which degrade RNA. RNAses are ubiquitous within the environment and it has been found that they are difficult to remove from solutions and containers used to isolate RNA.

While many nucleic acid purification procedures are well known and have been in existence for years, these procedures can be time consuming and may employ reagents that present dangers to those performing the purification. For example, it has long been known that DNA and RNA readily can be obtained in a purified form from a test sample using organic extraction procedures, but such procedures can require several extractions and therefore can be time consuming Additionally, the use of organic solvents is undesirable and dangerous if proper precautions are not followed.

Accordingly, there is a need for a safe, effective and convenient method for isolating nucleic acids from cells.

SUMMARY

The present disclosure relates to systems and methods for nucleic acid isolation from cellular samples. In particular, the present disclosure provides systems and methods for lysing cells and recovering nucleic acids.

Embodiments of the present invention provide compositions and methods for improved recovery of nucleic acids from biological samples.

For example, in some embodiments, the present invention provides a method of lysing cells, comprising: a) contacting a biological sample comprising a cell with a solution comprising beads and an aromatic solvent; and b) lysing the cells using a bead-beating device. In some embodiments, the sample is an aqueous biological fluid (e.g., including but not limited to, blood, blood products, or urine). In some embodiments, the solvent is toluene. In other embodiments, the solvent is a xylene (e.g., ortho-xylene, meta-xylene or para-xylene). In some embodiments, the solution further comprises a detergent (e.g., SDS) and/or a proteinase (e.g., PK). In some embodiments, the solvent is added at a concentration of 50 µl to 1 ml per 1 ml of sample. In some embodiments, the method further comprises the step of isolating nucleic acids from the sample following lysis. In some embodiments, nucleic acids are analyzed for the presence of a target DNA and/or RNA (e.g., a pathogen such as a virus, fungus or bacteria). In some embodiments, the analysis comprises, for example, a method selected from an amplification method, a sequencing method, or a hybridization method.

In some embodiments, the method is automated (e.g., by using robotic sample handling and analysis systems).

Further embodiments of the present invention provide kits and systems comprising components necessary, sufficient or useful for performing the described methods (e.g., reagents, controls, instructions, etc.).

BRIEF DESCRIPTION OF THE DRAWINGS

These and other features, aspects, and advantages of the present technology will become better understood with regard to the following drawings.

DETAILED DESCRIPTION

The present disclosure relates to systems and methods for nucleic acid isolation from cellular samples. In particular, the present disclosure provides systems and methods for lysing cells and recovering nucleic acids.

DEFINITIONS

To facilitate an understanding of the present technology, a number of terms and phrases are defined below. Additional definitions are set forth throughout the detailed description.

As used herein, "a" or "an" or "the" can mean one or more than one. For example, "a" widget can mean one widget or a plurality of widgets.

As used herein, the terms "subject" and "patient" refer to any animal, such as a dog, a cat, a bird, livestock, and particularly a mammal, and preferably a human.

As used herein, the term "sample" is used in its broadest sense. In one sense, it is meant to include a representative portion or culture obtained from any source, including biological and environmental sources. Biological samples may be obtained from animals (including humans) and encompass fluids, solids, tissues, and gases. Biological samples include blood products, such as plasma, serum, and the like. Environmental samples include environmental material such as surface matter, soil, mud, sludge, biofilms, water, and industrial samples. Such examples are not however to be construed as limiting the sample types applicable to the present invention.

Embodiments of the Technology

Although the disclosure herein refers to certain illustrated embodiments, it is to be understood that these embodiments are presented by way of example and not by way of limitation.

Embodiments of the present invention provide kits, systems and methods for cell lysis. For example, in some embodiments, the present invention provides methods for lysing cells (e.g., using bead-beating) in the presence of organic solvents (e.g., toluene, o-xylene, m-xylene, p-xylene).

Experiments conducted during the course of development of embodiments of the present invention demonstrated an increase in the amount of both bacterial (MRSA) and fungal (*Candida Albicans*) DNA recovery by inclusion of toluene and/or xylenes to a bead-beating process over a robust range of SDS and PK concentrations. The amount of background human DNA recovered remains constant in this process. This systems and methods described herein find use in diagnostic, research, screening and clinical applications that utilize the lysis of cells to obtain molecular information (e.g., pathogen identification, blood stream infections, biowarfare, microbial forensics, research use only products, vector borne illnesses, etc.).

Previous methods of bead-beating without addition of these solvents or other lysis methods involved solvents are considered the gold standard of cell lysis on the laboratory scale (See e.g., US20060148021 and Lett Appl. Microbiol. 1995 20:212; each of which is herein incorporated by reference in its entirety). The systems and methods of the present disclosure improve upon recovery of DNA exhibited in prior methods, for example, by a factor of two.

Accordingly, in some embodiments, the present invention provides systems, kits, and methods for lysis of cells.

The present invention is not limited to a particular sample. Examples of biological samples (e.g., aqueous samples) suitable for use with the described methods include, but are not limited to, whole blood, blood products (e.g., serum), urine, semen, lymph fluid, saliva, tears, mucus, etc.

The methods described herein are not limited to the lysis of a particular cell type. The systems and methods described herein are applicable to the lysis of any number of cells. In some embodiments, cells for lysis are eukaryotic cells (e.g., red or white blood cells). In some embodiments, eukaryotic cells or samples comprising eukaryotic cells are infected with pathogens (e.g., bacterial, viral or fungal pathogens). In other embodiments, cells for lysis are or include bacterial or fungal cells.

In some embodiments, pathogen or microorganism nucleic acids are recovered. In other embodiments, eukaryotic DNA from a subject is recovered.

Embodiments of the present invention provide compositions and methods for lysis of cells in the presence of solvents. The present invention is not limited to a particular solvent. In some embodiments, aromatic solvents are utilized. In some embodiments, the solvent is toluene, o-xylene, m-xylene or p-xylene. Additional solvents are contemplated to be within the scope of the present invention (e.g., including but not limited to, limonene, chloroform, 1-octanol, benzene or benzene like (e.g., polycyclic aromatic hydrocarbons (PAHs), e.g., naphthalene, anthracene, anthanthrene) or benzene/PAH derivatives (e.g., phenol, benzoic acid, ethyl benzene, trimehtylbenzene)).

The present invention is not limited to a particular lysis method. Methods of disruption vary according to the nature of the sample, and typically include autolysis (e.g., by incubation with toluene or a buffer), detergent lysis, pressure, enzymatic lysis (e.g., with lysozyme or β-glucanase), grinding, liquid nitrogen cooling bead-beating, or sonication.

The present disclosure is exemplified using a bead-beating method of disruption. However, the present invention is not limited to bead-beating. One of skill in the art recognizes that the methods and compositions described herein find use in a variety of mechanical disruption methods.

Bead-beating uses small glass, ceramic or steel beads and a high level of agitation by stirring or shaking of the mix. The method works well for all types of cellular material—from spores to animal and plant tissues. It has the advantage of being able to disrupt very small sample sizes and when processing many samples, to eliminate cross-contamination concerns.

At the simplest level of the method, an equal volume of beads are added to the cell or tissue suspension in a test tube and the sample is mixed on a common laboratory vortex mixer. While processing times are 3-10 times longer than that in specialty machines, it works for easily disrupted cells and is inexpensive.

In some embodiments, bead-beating is done in closed vials, centrifuge tubes, or sealed microtiter plates. The sample and 0.1 to 3 mm diameter beads are agitated at about 2000 oscillations per minute in a specially designed vial shaker driven by a high energy electric motor. Cell disruption is complete in 1-3 minutes of shaking. In some machines hundreds of samples can be processed simultaneously using deep well microplates.

Figure 6:
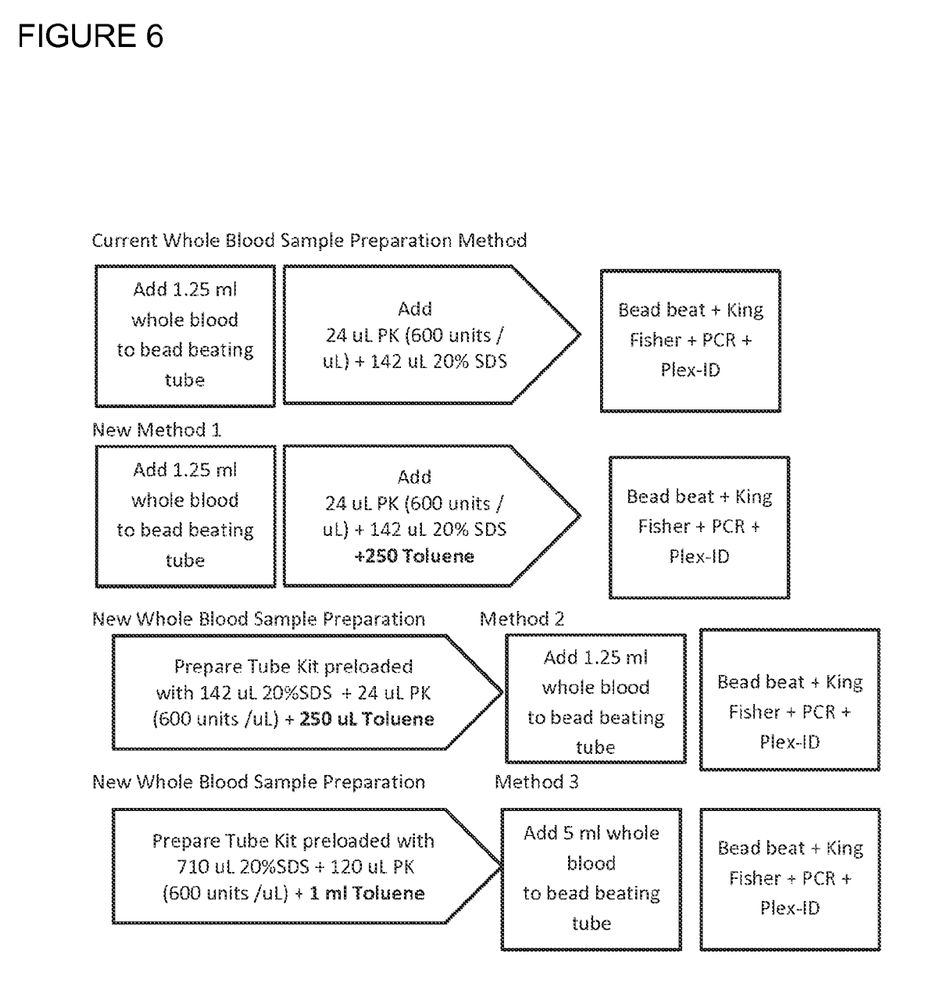
FIG. 6 shows a flow chart of exemplary methods of cell lysis utilized in embodiments of the present disclosure.

In some embodiments, bead-beating methods comprise the following steps: sample (e.g., blood or other biological fluid) is added to a bead-beating tube, proteinase (e.g., PK), detergent (e.g., SDS), and solvent (e.g., toluene) are added, and bead beating is performed using a laboratory designed or commercially available bead-beating device. FIG. 6 and Example 1 provide exemplary methods and formulations for performing cell lysis using methods of embodiments of the present invention.

In some embodiments, one or more steps are automated (e.g., using automated sample handling or robotics).

Following isolation, nucleic acids may be analyzed using any suitable method. In some embodiments, the presence of pathogens is detected (e.g., blood or urine borne pathogens). In other embodiments, the presence of nucleic acid variants, polymorphisms, mutations, etc. are detected.

The compositions and methods of embodiments of the present invention find use in a variety of research, clinical, screening, and therapeutic applications. Examples include, but are not limited to, detection of blood or urine borne pathogens, detection of biowarfare agents, microbial forensics, vector borne illness, and screening of pharmaceutical agents.

Examples of nucleic acid detection methods include, but are not limited to, sequencing, amplification, microarrays, probe binding and the like. Exemplary methods are described below.

A. Sequencing

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

A variety of nucleic acid sequencing methods are contemplated for use in the methods of the present disclosure including, for example, chain terminator (Sanger) sequencing, dye terminator sequencing, and high-throughput sequencing methods. Many of these sequencing methods are well known in the art. See, e.g., Sanger et al., Proc. Natl. Acad. Sci. USA 74:5463-5467 (1997); Maxam et al., Proc. Natl. Acad. Sci. USA 74:560-564 (1977); Drmanac, et al., Nat. Biotechnol. 16:54-58 (1998); Kato, Int. J. Clin. Exp. Med. 2:193-202 (2009); Ronaghi et al., Anal. Biochem. 242:84-89 (1996); Margulies et al., Nature 437:376-380 (2005); Ruparel et al., Proc. Natl. Acad. Sci. USA 102:5932-5937 (2005), and Harris et al., Science 320:106-109 (2008); Levene et al., Science 299:682-686 (2003); Korlach et al., Proc. Natl. Acad. Sci. USA 105:1176-1181 (2008); Branton et al., Nat. Biotechnol. 26(10):1146-53 (2008); Eid et al., Science 323:133-138 (2009); each of which is herein incorporated by reference in its entirety.

In some embodiments, the technology provided herein finds use in a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in *Genomics*, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques are known in the art, including fluorescence-based sequencing methodologies (See, e.g., Birren et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKernan et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., *Clinical Chem.*, 55: 641-658, 2009; MacLean et al., *Nature Rev.*

*Microbial.*, 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., Life Technologies/Ion Torrent, and Pacific Biosciences, respectively.

In pyrosequencing (Voelkerding et al., *Clinical Chem.*, 55: 641-658, 2009; MacLean et al., *Nature Rev. Microbial.*, 7: 287-296; U.S. Pat. Nos. 6,210,891; 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., *Clinical Chem.*, 55: 641-658, 2009; MacLean et al., *Nature Rev. Microbiol.*, 7: 287-296; U.S. Pat. Nos. 6,833,246; 7,115,400; 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. Nos. 5,912,148; 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, the technology finds use in nanopore sequencing (see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, the technology finds use in HeliScope by Helicos BioSciences (Voelkerding et al., *Clinical Chem.*, 55: 641-658, 2009; MacLean et al., *Nature Rev. Microbiol.*, 7: 287-296; U.S. Pat. No. 7,169,560; U.S. Pat. Nos. 7,282,337; 7,482,120; 7,501,245; 6,818,395; 6,911,345; 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~400 Mb generated per run. The read-length is 100 base pairs. The accuracy for homopolymer repeats of 5 repeats in length is ~98%. The benefits of ion semiconductor sequencing are rapid sequencing speed and low upfront and operating costs.

The technology finds use in another nucleic acid sequencing approach developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., *Clinical Chem.*, 55: 641-58, 2009; U.S. Pat. No. 7,329,492; U.S. patent application Ser. Nos. 11/671,956; 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

B. Hybridization

Illustrative non-limiting examples of nucleic acid hybridization techniques include, but are not limited to, microarrays including, but not limited to: DNA microarrays (e.g., cDNA microarrays and oligonucleotide microarrays). A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes or transcripts by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

C. Amplification

Nucleic acids may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399,491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPaS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

D. Detection Methods

Non-amplified or amplified nucleic acids can be detected by any conventional means. For example, the nucleic acids can be detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety).

In some embodiments, nucleic acids are detected and characterized by the identification of a unique base composition signature (BCS) using mass spectrometry (e.g., Abbott PLEX-ID system, Abbot Ibis Biosciences, Abbott Park, Ill.,) described in U.S. Pat. Nos. 7,108,974, 8,017,743, and 8,017, 322; each of which is herein incorporated by reference in its entirety.

In some embodiments, a computer-based analysis program is used to translate the raw data generated by the detection assay (e.g., the presence, absence, or amount of a given nucleic acid) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., presence or absence of a nucleic acid) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action.

E. Systems and Kits

In some embodiments, the present invention provides kits and systems for the lysis, isolation, and analysis of nucleic acids (e.g., DNA and/or RNA). In some embodiments, kits include reagents necessary, sufficient or useful for detection of nucleic acids (e.g., reagents, controls, instructions, etc.). In some embodiments, systems include automated sample and reagent handling devices (e.g., robotics).

In some embodiments, kits include components for cell lysis using bead-beating (e.g., proteinase, solvent, detergent, buffer) in a single tube or container. The end-user simply adds a biological sample and performs the assay.

EXPERIMENTAL

The following examples are provided in order to demonstrate and further illustrate certain preferred embodiments and aspects of the present invention and are not to be construed as limiting the scope thereof.

Example 1

A. Fluorinated ZY Beads
Purpose:
To examine the performance of Fluorinated ZY Beads.
Conclusion:
Increased concentration in fluorination did not improve *Candida* & MRSA signal.
Materials and Methods:
Whole Blood.
MRSA CDC6 $1.0 \times 10^7$ & *C. albicans* $1.0 \times 10^6$
Table 1 shows a layout of samples and conditions.

TABLE 1

|   | 1 | 2  | 3  | 4  | 5  | 6    | 7 | 8  | 9  | 10 | 11 | 12     |
|---|---|----|----|----|----|------|---|----|----|----|----|--------|
| A | 1 | 9  | 17 | 25 | 33 | 41   | 1 | 9  | 17 | 25 | 33 | 41     |
| B | 2 | 10 | 18 | 26 | 34 | 42   | 2 | 10 | 18 | 26 | 34 | 42     |
| C | 3 | 11 | 19 | 27 | 35 | NTC  | 3 | 11 | 19 | 27 | 35 | NTC    |
| D | 4 | 12 | 20 | 28 | 36 | MRSA | 4 | 12 | 20 | 28 | 36 | Can-   |
| E | 5 | 13 | 21 | 29 | 37 |      | 5 | 13 | 21 | 29 | 37 | dida   |
| F | 6 | 14 | 22 | 30 | 38 | NAC  | 6 | 14 | 22 | 30 | 38 | NAC    |
| G | 7 | 15 | 23 | 31 | 39 | MRSA | 7 | 15 | 23 | 31 | 39 | Can-   |
| H | 8 | 16 | 24 | 32 | 40 |      | 8 | 16 | 24 | 32 | 40 | dide   |

Table 2 shows Q-PCR setup

TABLE 2

| Q-PCR Setup: | | | | | |
|---|---|---|---|---|---|
| Ba | # rxx | 58 | MRSA & *Candida* | | |
| with IPC | total volume | 1450 | 25 | ul/rx | |
|  | cocktail | 1160 | 20 | ul mix/rx | |
|  | water | 246.5 | x | | |
|  | 2X | 725.0 | | uM stocks | final uM |
|  | probe | 5.8 | | probe | 0.2 |
|  | forward | 4.4 | | forward | 0.3 |
|  | reverse | 4.4 | | reverse | 0.3 |
|  | 10X IPC Mix | 145 | | | |
|  | 50X IPC Template | 29 | 986 | volume check | |

Procedure:
500 CFU/ml of MRSA & 60 CFU/ml of *Candida* was spiked into 100 ml of blood.
MRSA was diluted down to $1.0 \times 10^5$ and *Candida* was diluted down to $1.0 \times 10^4$ and 500 μl of MRSA & 600 μl of *C. albicans* was spiked into 100 ml of whole blood.
1.25 ml of spiked blood was spiked with 25 μl of PK, 142 μl of 20% SDS.
Control Samples were processed according to the current protocol.

Following sample isolation Q-PCR targeting of MRSA & *Candida* was executed.

Figure 1:
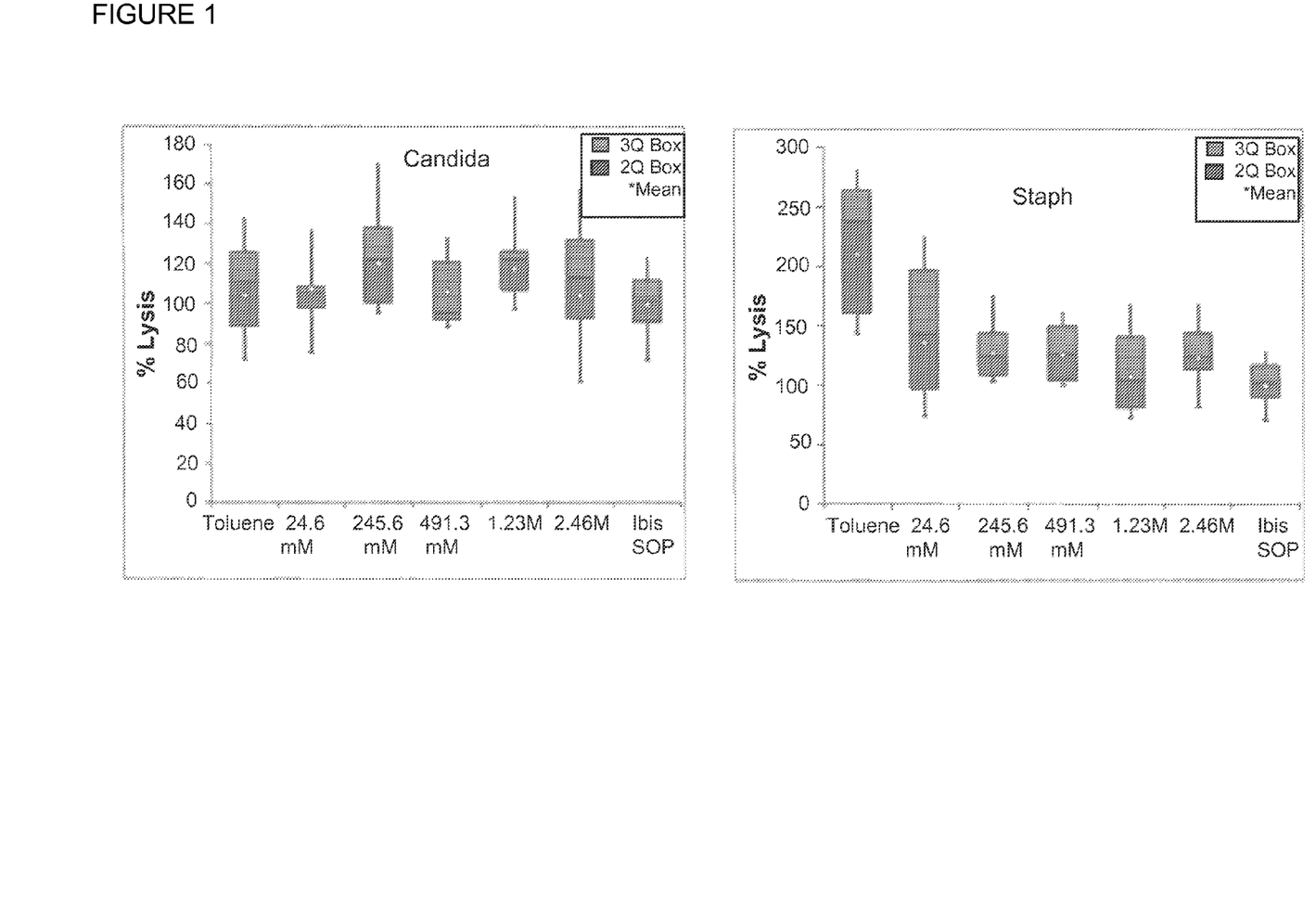
FIG. 1 recovery of *Candida* and MRSA in the presence of fluorinated ZY beads.
Figure 2:
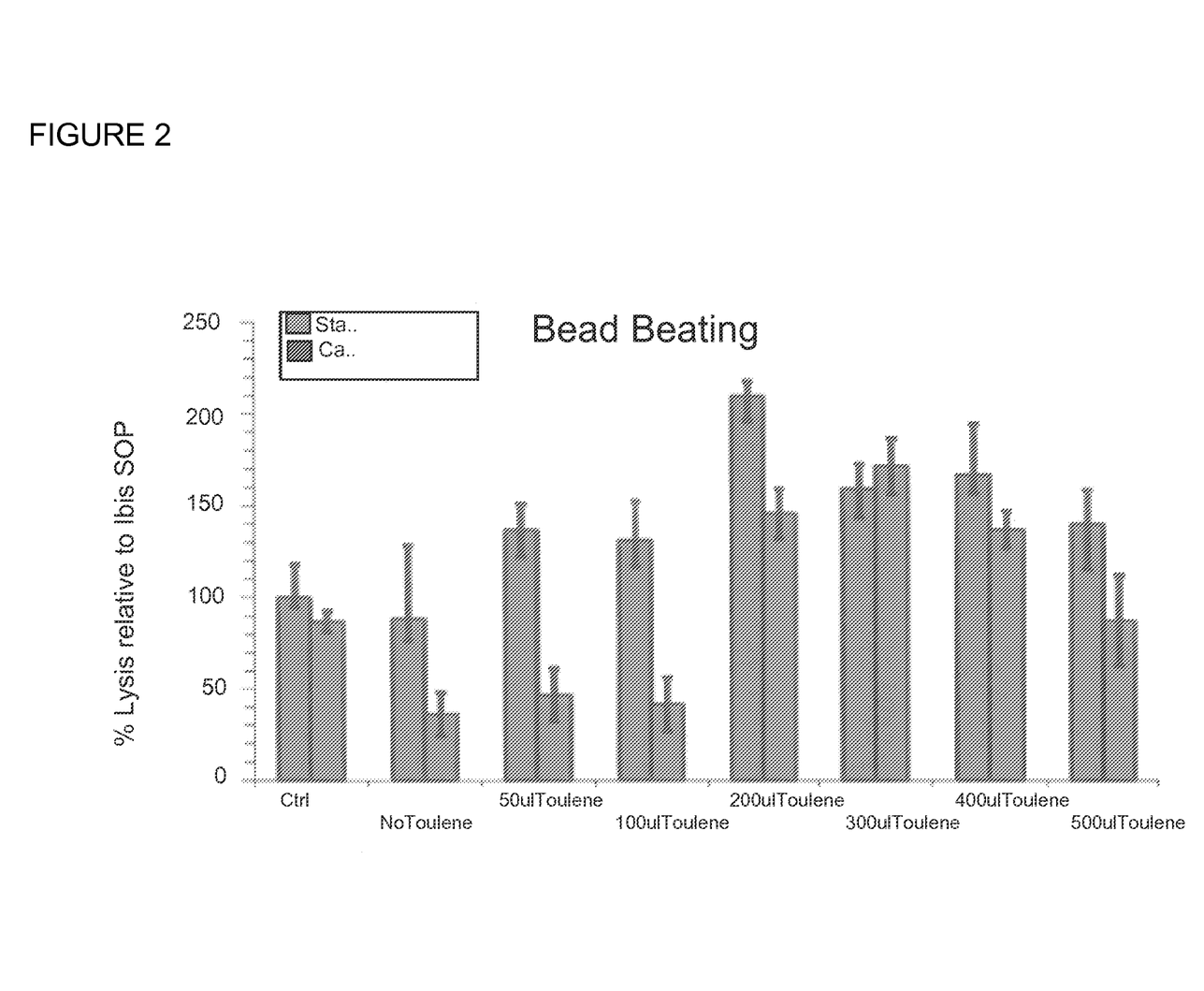
FIG. 2 shows recovery of *Candida* and MRSA after lysis in the presence of toluene.
Figure 3:
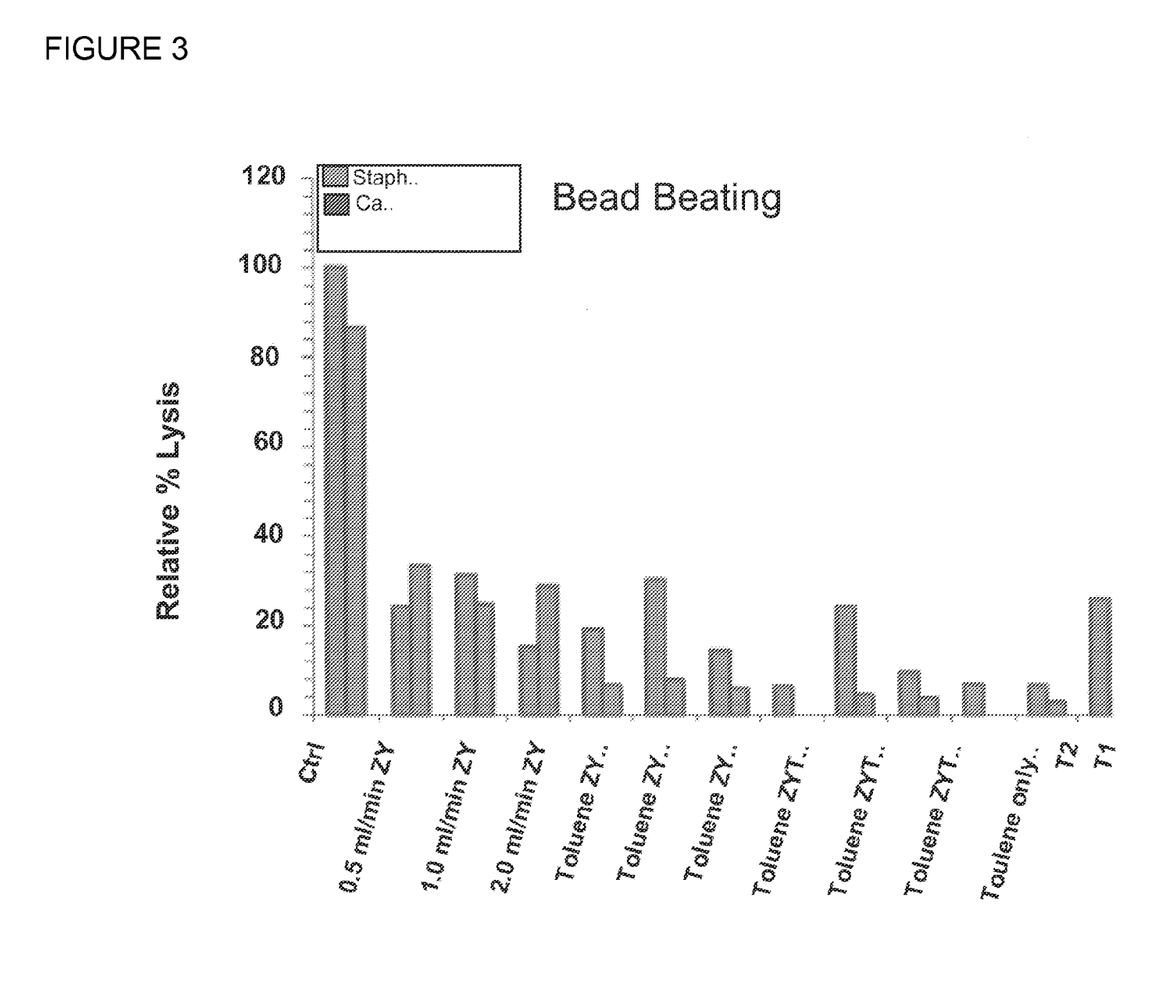
FIG. 3 shows recovery of *Candida* and MRSA after lysis in the presence of toluene.
Figure 4:
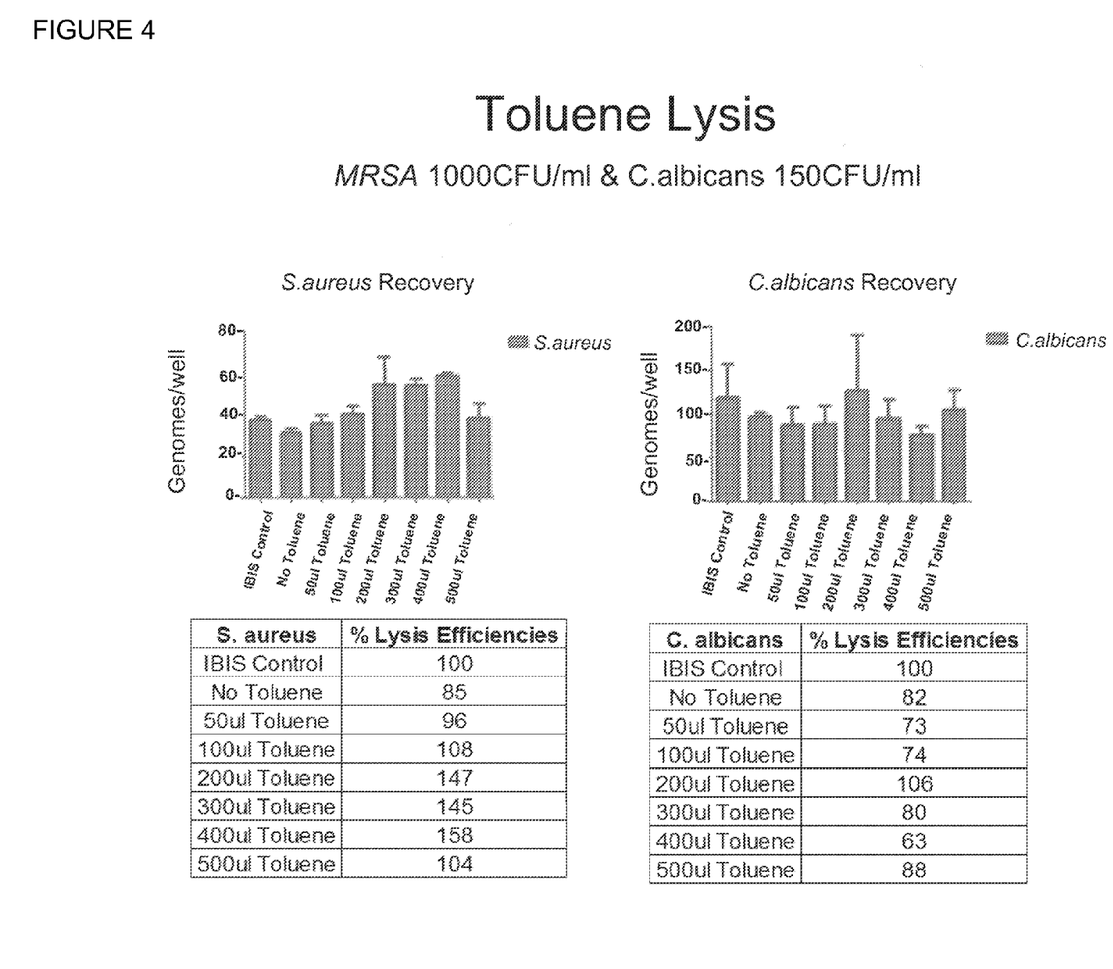
FIG. 4 shows recovery of *Candida* and MRSA after lysis in the presence of toluene.

Results are shown in FIG. 1. Increased concentration in fluorination did not improve *Candida* & MRSA signal.

B. Toluene Lysis in Whole Blood

Purpose:

To investigate lysis efficiency of Toluene in whole blood.

Conclusions:

Lysis efficiency of toluene in whole blood was better than the standard Bead Beating protocol.

Materials and Methods:

Whole Blood.

MRSA CDC6 $1.0 \times 10^7$ & *C. albicans* $1.0 \times 10^6$

Table 3 shows layout of samples and conditions.

TABLE 3

|   | 1 | 2 | 3 | 4 | 5 | 6 | 7 | 8 | 9 | 10 | 11 | 12 |
|---|---|---|---|---|---|---|---|---|---|----|----|----|
| A | 1 | 9 | 17 |   |   |      | 1 | 9 | 17 |   |   |         |
| B | 2 | 10 | 18 |  |   |      | 2 | 10 | 18 |  |   |         |
| C | 3 | 11 | 19 |  |   | NTC  | 3 | 11 | 19 |  |   | NTC     |
| D | 4 | 12 | 20 |  |   | MRSA | 4 | 12 | 20 |  |   | Candida |
| E | 5 | 13 | 21 |  |   |      | 5 | 13 | 21 |  |   |         |
| F | 6 | 14 | 22 |  |   |      | 6 | 14 | 22 |  |   |         |
| G | 7 | 15 | 23 |  |   |      | 7 | 15 | 23 |  |   |         |
| H | 8 | 16 | 24 |  |   |      | 8 | 16 | 24 |  |   |         |

1 Ctrl
2 Ctrl
3 Ctrl
4 No Toulene
5 No Toulene
6 No Toulene
7 50 µl Toluene
8 50 µl Toluene
9 50 µl Toluene
10 100 µl Toluene
11 100 µl Toluene
12 100 µl Toluene
13 200 µl Toluene
14 200 µl Toluene
15 200 µl Toluene
16 300 µl Toluene
17 200 µl Toluene
18 200 µl Toluene
19 400 µl Toluene
20 400 µl Toluene
21 400 µl Toluene
22 500 µl Toluene
23 500 µl Toluene
24 500 µl Toluene
1 ZY 0.5 ml/min
2 ZY 0.5 ml/min
3 ZY 0.5 ml/min
4 ZY 1.0 ml/min
5 ZY 1.0 ml/min
6 ZY 1.0 ml/min
7 ZY 2.0 ml/min
8 ZY 2.0 ml/min
9 ZY 2.0 ml/min
10 ZYT 0.5 ml/min
11 ZYT 0.5 ml/min
12 ZYT 0.5 ml/min
13 ZYT 1.0 ml/min
14 ZYT 1.0 ml/min
15 ZYT 1.0 ml/min
16 ZYT 2.0 ml/min
17 ZYT 2.0 ml/min
18 ZYT 2.0 ml/min
19 Toulene only & Blood
20 Toulene only & 20 Blood
21 T2
22 T2
23 T1
24 T1
Toluene: 30 ml blood into 15 ml toluene.
T2: 2 ml toluene & 10 ml of blood.
T1: 1 ml toluene & 10 ml of blood.
PCR Formulations are shown in Table 4:

TABLE 4

| Ba | # rxx | 34 | MRSA & Candida | | |
|---|---|---|---|---|---|
| with IPC | total volume | 850 | 25 | ul/rx | |
|   | cocktail | 680 | 20 | ul mix/rx | |
|   | water | 144.5 | x | | |
|   | 2X | 425.0 | | uM stocks | final uM |
|   | probe | 3.4 | | probe | 0.2 |
|   | forward | 2.6 | | forward | 0.3 |
|   | reverse | 2.6 | | reverse | 0.3 |
|   | 10X IPC Mix | 85 | | | |
|   | 50X IPC | 17 | 578 | volume check | |
|   | Template | | | | |

Procedure:

1000 CFU/ml of MRSA & 150 CFU/ml of *Candida* was spiked into 44.125 ml of blood.

MRSA was diluted down to $1.0 \times 10^5$ and *Candida* was diluted down to $1.0 \times 10^4$ and 441.3 µl of MRSA & 662 µl of *Candida* was spiked into 44.125 ml of whole blood.

44.125 ml of blood was spiked with 882.5 µl of PK and 5.0 ml of 20% SDS.

1 ml of blood sample was processed according to the standard bead beating protocol.

Toluene/blood mixtures after lysis were viscous.

Figure 5:
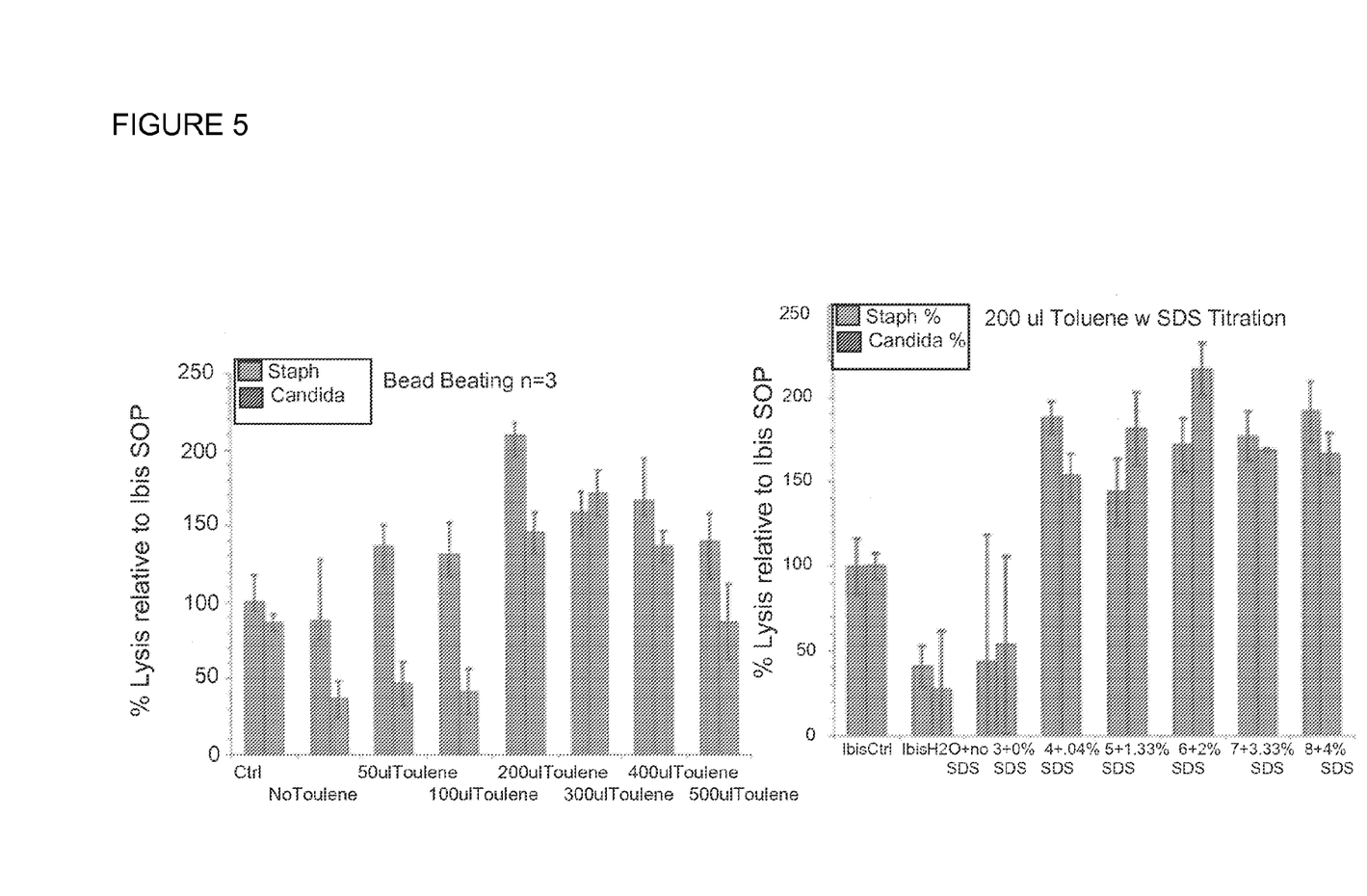
FIG. 5 shows recovery of *Candida* and MRSA after lysis in the presence of toluene or ortho-xylene.

Results are shown in FIGS. 2-5. The results indicate that the lysis efficiency of toluene in whole blood was better than the standard bead beating protocol. FIG. 5 shows a a summary of improved cell lysis/DNA recovery for the toluene addition experiments, SDS titration with toluene, PK titration with toluene, and xylene titrations.

C. Results

Initial experiments were conducted on a 1 ml whole blood sample with dodecylsulfate (SDS) and proteinase K (PK). To this blood, Toluene was titrated from 0-500 µL with a balance of water being added to bring the total a total sample volume of 1.5 ml. The samples with toluene were placed in a standard beat beating system, such as the Bertin Precellys (Bertin Technologies, Montigny-le-Bretonneux, France) and compared to a standard procedure with 1 ml of blood and a second control of the same procedure with 500 µL of $H_2O$ added. The minimum amount added (50 µL) was found to improve recovery of Staph (136%) with the best overall conditions being 200 or 300 µL of toluene added to provide 210% improvement in Staph and 170% in *Candida* DNA recovery.

Further experiments titrated the amount of SDS (from 0-4 wt %) in the system (1 ml blood with PK and 200 µL toluene with total volume 1.5 ml) and found that the minimum amount of SDS, 0.6 wt % of SDS, yielded these positive results (while the 0% SDS case was difficult to pipette and would require centrifugation after bead beating). For these titration experiments that average improvement was 174% for Staph and 177% for *Candida* (n=15 for each organism). A titration of proteinase K (PK) was performed in the system with 1 ml of whole blood, 2% SDS, 200 µL toluene and a total volume of 1.5 ml. When PK was omitted the sample was difficult to pipette and would require a centrifugation step to recover the supernatant. With as little as 5 µL of PK and robust through 100 µL of PK added (600 units/µL), improved performance with an average improvement of 217% and 220% for Staph and *Candida* respectively (n=15 for both organisms) was observed.

Similar titrations with a wide variety of other organic solvents (e.g., methanol, ethanol, isopropanol, DMSO, acetonitrile, formamide, dimethylformamide) resulted in no improvements in DNA recovery. Ortho-xylene demonstrated improved results compared to bead beating without the xylene.

D. Formulations

Exemplary formulations for use with 1 ml of whole blood are provided below. The values may be scaled accordingly. Additionally the amount of toluene is optionally varied from 50-400 µL/mL of whole blood and the bead mass may be altered or chemical altered (e.g., ZO beads instead of ZY or Tungsten beads instead of ZY beads).

Formulation Example 1 (1 ml blood volume, high toluene/SOS/PK concentration)
1 ml of whole blood or EDTA treated whole blood
0.95 grams ZY beads
250 µL Toluene
150 µL 20% SDS solution
25 µL of 600 units/µL Proteinase K Formulation Example 2 (1.25 ml blood volume, high toluene/SOS/PK concentration)
1.25 ml of whole blood or EDTA treated whole blood
0.95 grams ZY beads
100 µL Toluene
150 µL 20% SDS solution
25 µL of 600 units/µL Proteinase K Formulation Example 3 (1.25 ml blood volume, reduced SOS/PK concentrations)
1.25 ml of whole blood or EDTA treated whole blood
0.95 grams ZY beads
200 µL Toluene
40 µL 20% SDS solution
5 µL of 600 units/µL Proteinase K Formulation Example 4 (5 ml blood volume with toluene)
5 ml of whole blood or EDTA treated whole blood
3.8 grams ZY beads
800 µL Toluene
320 µL 20% SDS solution
20 µL of 600 units/µL Proteinase K Formulation Example 5 (xylene instead of toluene 1.25 ml blood volume)
1.25 ml of whole blood or EDTA treated whole blood
0.95 grams ZY beads
200 µL Xylene
40 µL 20% SDS solution
5 µL of 600 units/µL Proteinase K Formulation Example 6(xylene instead of toluene 5 ml blood volume)
5 ml of whole blood or EDTA treated whole blood
3.8 grams ZY beads
800 µL Xylene
320 µL 20% SDS solution
20 µL of 600 units/µL Proteinase K All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of lysing cells, comprising:
   a) contacting an aqueous biological fluid sample comprising a cell with a solution comprising beads and an aromatic solvent wherein said solvent is selected from the group consisting of toluene, ortho-xylene, meta-xylene and para-xylene; and
   b) lysing said cells using a bead-beating device.

2. The method of claim 1, wherein said aqueous biological fluid is selected from the group consisting of blood, blood products, and urine.

3. The method of claim 1, wherein said solution further comprises a detergent and/or a proteinase.

4. The method of claim 3, wherein said detergent is sodium dodecyl sulfate (SDS).

5. The method of claim 3, wherein said proteinase is proteinase K (PK).

6. The method of claim 1, wherein said solvent is added at a concentration of 50 µl to 1 ml per 1 ml of sample.

7. The method of claim 1, further comprising the step of isolating nucleic acids from said sample following said lysing.

8. The method of claim 7, further comprising the step of analyzing said nucleic acids for ample for the presence of a target DNA and/or RNA.

9. The method of claim 8, wherein said target nucleic acid is a pathogen.

10. The method of claim 9, wherein said pathogen is selected from the group consisting of a virus, a fungus, and a bacterium.

11. The method of claim 8, wherein said analyzing comprises a method selected from the group consisting of an amplification method, a sequencing methods, and a hybridization method.

* * * * *